(12) United States Patent
Adachi

(10) Patent No.: US 9,080,961 B2
(45) Date of Patent: Jul. 14, 2015

(54) METHOD FOR DETECTING WATER IN PLASTICS AND WATER REMOVAL SYSTEM FOR PLASTIC MATERIALS

(75) Inventor: Yukimasa Adachi, Aichi (JP)

(73) Assignee: Nakamura Kagakukogyo Co., Ltd., Aichi (JP)

( * ) Notice: Subject to any disclaimer, the term of this patent is extended or adjusted under 35 U.S.C. 154(b) by 157 days.

(21) Appl. No.: 13/806,744

(22) PCT Filed: Oct. 5, 2011

(86) PCT No.: PCT/JP2011/072935
§ 371 (c)(1),
(2), (4) Date: Feb. 26, 2013

(87) PCT Pub. No.: WO2012/046756
PCT Pub. Date: Apr. 12, 2012

(65) Prior Publication Data
US 2013/0212904 A1  Aug. 22, 2013

(30) Foreign Application Priority Data
Oct. 6, 2010 (JP) ................. 2010-226249

(51) Int. Cl.
*F26B 25/22* (2006.01)
*G01N 21/3554* (2014.01)
(Continued)

(52) U.S. Cl.
CPC ............ *G01N 21/3554* (2013.01); *B29B 13/08* (2013.01); *F26B 25/22* (2013.01); *G01N 21/3581* (2013.01); *B29B 13/065* (2013.01)

(58) Field of Classification Search
CPC ..................................................... F26B 17/12
USPC .......... 34/245, 255, 259, 262, 266, 275, 264; 219/121.11, 121.13, 121.14, 679; 250/339; 392/407; 73/655
See application file for complete search history.

(56) References Cited

U.S. PATENT DOCUMENTS 4,567,340 A * 1/1986 Latchum, Jr. ................. 219/701
5,789,750 A   8/1998 Nuss
(Continued)

FOREIGN PATENT DOCUMENTS

JP   2000-263549   9/2000
JP   2004-308928   11/2004
(Continued)

OTHER PUBLICATIONS

P. Parasoglou et al., "Quantitative Moisture Content Detection in Food Wafers," Proc. 34th Int'l Conf. on Infrared, Millimeter and Terahertz waves, Sep. 2009, Busan, Korea.
(Continued)

*Primary Examiner* — Steve M Gravini
(74) *Attorney, Agent, or Firm* — Martine Penilla Group, LLP

(57) ABSTRACT

[Object] To provide a method for detecting water in plastics and a water removal system for plastic materials that enable an amount of water contained in a plastic to be measured accurately and rapidly.
[Solution Means] A plastic 13 of known moisture state is irradiated with electromagnetic waves of a bandwidth of 50 GHz to 1000 GHz from an oscillating apparatus 11 and remaining electromagnetic waves not absorbed by the plastic 13 are received and measured by a receiver 12 to acquire a first measurement value in advance. The plastic 13 of unknown moisture state is then irradiated with the electromagnetic waves of the bandwidth of 50 GHz to 1000 GHz from the oscillating apparatus and the remaining electromagnetic waves not absorbed by the plastic 13 are received and measured by the receiver 12 to acquire a second measurement value. The first measurement value and the second measurement value are compared to compute the moisture state of the plastic of unknown moisture state.

18 Claims, 4 Drawing Sheets

(51) Int. Cl.
*B29B 13/08* (2006.01)
*G01N 21/3581* (2014.01)
*B29B 13/06* (2006.01)

(56) References Cited

U.S. PATENT DOCUMENTS

| | | | | |
|---|---|---|---|---|
| 6,035,546 | A * | 3/2000 | Stricker et al. | 34/266 |
| 6,098,306 | A * | 8/2000 | Ramsey et al. | 34/257 |
| 6,163,976 | A * | 12/2000 | Tada et al. | 34/72 |
| 6,233,841 | B1 * | 5/2001 | Beach | 34/262 |
| 6,247,246 | B1 * | 6/2001 | Scalese et al. | 34/259 |
| 6,618,957 | B2 * | 9/2003 | Novak et al. | 34/264 |
| 7,148,455 | B2 * | 12/2006 | Scalese et al. | 219/679 |
| 8,196,312 | B2 * | 6/2012 | Taguchi | 34/443 |
| 8,516,714 | B2 * | 8/2013 | Biemans et al. | 34/284 |
| 8,776,390 | B2 * | 7/2014 | Hanaoka et al. | 34/168 |
| 8,793,900 | B2 * | 8/2014 | Moretto | 34/381 |
| 8,826,558 | B2 * | 9/2014 | Priebe et al. | 34/60 |
| 8,839,527 | B2 * | 9/2014 | Ben-Shmuel et al. | 34/260 |
| 8,844,158 | B2 * | 9/2014 | Dehn | 34/381 |
| 2002/0046474 | A1 * | 4/2002 | Novak et al. | 34/259 |
| 2010/0115785 | A1 * | 5/2010 | Ben-Shmuel et al. | 34/260 |

FOREIGN PATENT DOCUMENTS

| | | |
|---|---|---|
| JP | 2007-003485 | 1/2007 |
| JP | 2010-204035 | 9/2010 |
| JP | 2012078304 A * | 4/2012 |

OTHER PUBLICATIONS

J.A. Hejase et al., "Terahertz Packaging: Study of Substrates for Novel Component Designs," Proc. 60th Elec. Comp. and Tech. Conf. (ECTC), Jun. 2010, Las Vegas, NV.

S. Wietzke et al., "Terahertz Spectroscopy: A Powerful Tool for the Characterization of Plastic Materials," 2010 10th IEEE Int. Conf. On Solid Dielectrics (ICSD), Jul. 4-9, 2010, Potsdam, Germany (pp. 1-4).

English translations of various Office Actions issued in corresponding Japanese Application No. 2010-226249 (25 total pages), Apr. 2014.

* cited by examiner

METHOD FOR DETECTING WATER IN PLASTICS AND WATER REMOVAL SYSTEM FOR PLASTIC MATERIALS

BACKGROUND OF THE INVENTION

1. Field of the Invention

The present invention relates to a method for detecting water in plastics using electromagnetic waves of a predetermined bandwidth and to a water removal system for plastic materials that implements the detecting method.

2. Description of Related Art

Generally, highly hygroscopic plastic materials for plastic molding are handled so as to avoid contact with air as much possible in performing molding and are removed of already-contained water by performing a heat treatment in a pre-feeding process. This is because when a molded product is molded using a moisture-absorbed plastic material as it is, an outer surface of the product becomes roughened or pores form due to a vaporization action of water attendant to heating. On the other hand, there are cases where a plastic must contain some amount of water from an aspect of product quality. That is, it is important to control a plastic to be in a favorable moisture state from a material stage to a product stage.

Conventionally, the amount of water in a plastic is generally measured by a Karl Fischer method. In comparison to a loss-on-drying method, with which a change in weight due to volatilization of water is measured, the Karl Fischer method enables detection of water specifically and is thus more accurate as a method for measuring the amount of water. As arts of measuring water by the Karl Fischer method, Patent Documents 1 and 2 are cited below.

Patent Document 1: Japanese Published Unexamined Patent Application No. H05-4716
Patent Document 2: Japanese Published Unexamined Patent Application No. H09-33484

DISCLOSURE OF THE INVENTION

Object(s) of the Invention

However, the Karl Fischer method is a classical method of measuring water in a sample by coulometric or volumetric titration using iodine, sulfur dioxide, alcohol, etc., and although high in the accuracy of measurement values, it takes time and trouble and is not a method that enables real-time measurement. A method by which an amount of water contained in a plastic can be measured accurately and rapidly was thus demanded.

The present invention was made to resolve the above issue and an object thereof is to provide a method for detecting water in plastics and a water removal system for plastic materials that enable an amount of water contained in a plastic to be measured accurately and rapidly.

SUMMARY OF THE INVENTION

To achieve the above object, according to the gist of a first aspect of the present invention, a plastic of known moisture state is irradiated with electromagnetic waves of a bandwidth of 50 GHz to 1000 GHz from an oscillating apparatus, remaining electromagnetic waves not absorbed by the plastic are measured to acquire a first measurement value in advance, the plastic of unknown moisture state or a plastic of unknown moisture state different from the plastic (hereinafter these shall be referred to as the "measured plastic") is irradiated with the electromagnetic waves of the bandwidth of 50 GHz to 1000 GHz from the oscillating apparatus, the remaining electromagnetic waves not absorbed by the measured plastic are measured to acquire a second measurement value, and the first measurement value and the second measurement value are compared to compute the moisture state of the plastic of unknown moisture state.

Also, according to the gist of a second aspect of the present invention, plastics of the same type that are of known moisture states and are of at least two different kinds of moisture states are respectively irradiated with electromagnetic waves of a bandwidth of 50 GHz to 1000 GHz from an oscillating apparatus, remaining electromagnetic waves not absorbed by the plastics are measured to acquire a plurality of first measurement values in advance, a function is derived from a relationship between the plurality of first measurement values acquired and the plurality of moisture states, the plastic of unknown moisture state or a plastic of unknown moisture state different from the plastic (hereinafter these shall be referred to as the "measured plastic") is irradiated with the electromagnetic waves of the bandwidth of 50 GHz to 1000 GHz from the oscillating apparatus, the remaining electromagnetic waves not absorbed by the measured plastic are measured to acquire a second measurement value, and the second measurement value is applied to the function to compute the moisture state corresponding to the plastic of unknown moisture state.

Also, according to the gist of a third aspect of the present invention, in addition to the arrangement of the first aspect or second aspect of the present invention, the first or second measurement value is measured by making the electromagnetic waves generated from the oscillating apparatus be transmitted through the plastic and be received by a receiving apparatus disposed at a rear side of the plastic.

Also, according to the gist of a fourth aspect of the present invention, in addition to the arrangement of the first aspect or second aspect of the present invention, the first or second measurement value is measured by making the electromagnetic waves generated from the oscillating apparatus be reflected inside the plastic and making the reflected waves be received by a receiving apparatus.

Also, according to the gist of a fifth aspect of the present invention, in addition to the arrangement of the first aspect or second aspect of the present invention, the first or second measurement value is measured by making the electromagnetic waves generated from the oscillating apparatus be scattered inside the plastic and making the scattered waves be received by a receiving apparatus.

With the arrangement of the first aspect, first, the plastic of known moisture state (hereinafter, this plastic shall be referred to as the "reference plastic") is irradiated with the electromagnetic waves of the bandwidth of 50 GHz to 1000 GHz from the oscillating apparatus and by measuring the remaining electromagnetic waves not absorbed by the plastic, the first measurement value corresponding to the moisture state of the plastic can be acquired. The above range is of a wavelength bandwidth in which terahertz waves and millimeter waves belong. The moisture state can normally be expressed by a numerical value, such as a moisture percentage, moisture content, etc. The first measurement value is acquired in advance as a reference value. Knowing of the moisture state can be realized, for example, by use of a Karl Fischer method, which enables quantification of water in plastics. For example, suppose there is a set of plastic of a certain lot of substantially uniform but unknown moisture states. By sampling a portion of the plastic and measuring the amount of water by the Karl Fischer method, the moisture states of that set of plastic can be ascertained. By then irradiating the electromagnetic waves onto the plastic (reference plastic) with which the moisture state has thus become known and measuring the remaining electromagnetic waves, a relationship between the amount of water and the remaining electromagnetic waves (first measurement value) is obtained.

Thereafter, a plastic, which is of the same material as the reference plastic but is of unknown moisture state, or a plastic of different material from the reference plastic (hereinafter, this plastic shall be referred to as the "measured plastic") is irradiated with the electromagnetic waves of the above bandwidth from the oscillating apparatus and the remaining electromagnetic waves not absorbed by the plastic is measured to likewise obtain the second measurement value. The second measurement value and the first measurement value are then compared. That is, the moisture state of the plastic of unknown moisture state is estimated based on the second measurement value and using the first measurement value as a reference. Generally in converting to data, a difference is obtained.

Here, if the second measurement value is measured under the same conditions as the first measurement value and is equal to the first measurement value, the measured plastic can be said to be the same in moisture state as the reference plastic. Also, if the values are the same within a margin of error, the measured plastic may, although depending on the purpose of use, be handled in a manner similar to the reference plastic. Even if the plastics differ in composition, measurement is made possible by providing a coefficient that enables the use of the first measurement value. Further, a product check can be performed because it can be made known from the measurement value that the moisture percentage is lower or oppositely the moisture percentage is higher than the reference plastic.

With the arrangement of the second aspect, first, each of the reference plastics of at least two different kinds is irradiated with the electromagnetic waves of the bandwidth of 50 GHz to 1000 GHz from the oscillating apparatus and by measuring the remaining electromagnetic waves not absorbed by the plastics, the plurality of first measurement value corresponding to the moisture states can be acquired, and a function can be derived from the relationship between the plurality of first measurement values and the plurality of moisture states. As a means for obtaining the plurality of first measurement values, for example, the above-described Karl Fischer method may be considered.

Thereafter, the measured plastic is irradiated with the electromagnetic waves of the same bandwidth from the oscillating apparatus and the remaining electromagnetic waves not absorbed by the plastic are measured to likewise obtain the second measurement value. The second measurement value is then applied to the function to compute the moisture state corresponding to the measured plastic. It thus becomes possible to judge the moisture state of the measured plastic based on a position of the second measurement value on the function, or any point on the function may be used as a reference value and the moisture state can be judged based on a relationship of the second measurement value with respect to the reference point.

For example, suppose a first-order function, expressed by $f(x)=ax+b$, is derived based on the plurality of first measurement values. By substituting the second measurement value in x, the $f(x)$ that is the moisture state of the plastic of unknown moisture state is determined. Also, by judging whether the second measurement value is large or small with respect to a reference value on $f(x)$ that is not a first measurement value, a product check can be performed because it can be made known that the moisture percentage is lower or oppositely the moisture percentage is higher than the reference value.

A method may be considered where, in the first or second aspect of the present invention, arrangements are made so that the electromagnetic waves of a bandwidth of 50 GHz to 1000 GHz generated from the oscillating apparatus are transmitted through the plastic and received by a receiving apparatus disposed at a rear side of the plastic to measure the remaining electromagnetic waves. With this method, the oscillating apparatus and the receiving apparatus can be disposed respectively at a front side and the rear side provided that there is space at each side. Also, the electromagnetic waves of the bandwidth of 50 GHz to 1000 GHz generated from the oscillating apparatus may be made to reflect inside the plastic and the reflected waves may be received by the receiving apparatus, or the electromagnetic waves generated from the oscillating apparatus may be made to scatter inside the plastic and the scattered waves may be received by the receiving apparatus. Such arrangements are especially advantageous in a case where there is a spatial restriction.

Positioning of a lens for condensing the electromagnetic waves along a path or positioning of a reflecting mirror for changing the path may be carried out freely as necessary.

Also, the plastic that is to be the object of measurement in the present invention conceptually includes both thermoplastic and thermosetting plastics as well as elastomers.

Also, according to the sixth aspect of the present invention, a water removal system for plastic materials, receiving a supply of a fixed amount of a plastic material at a time, performing a heat treatment on the plastic material inside a treatment container to remove water inside the plastic material, and conveying the plastic material downstream according to treatment unit, is arranged so that a plastic material of known moisture state is housed in a measurement passage disposed at a downstream position of the treatment container and irradiated with electromagnetic waves of a bandwidth of 50 GHz to 1000 GHz from an oscillating apparatus, remaining electromagnetic waves not absorbed by the plastic material are measured to acquire a first measurement value in advance, the plastic of unknown moisture state or a plastic material of unknown moisture state different from the plastic (hereinafter these shall be referred to as the "measured plastic material") is irradiated in the measurement passage with the electromagnetic waves of the bandwidth of 50 GHz to 1000 GHz from the oscillating apparatus, the remaining electromagnetic waves not absorbed by the measured plastic material are measured to acquire a second measurement value, and the first measurement value and the second measurement value are compared to compute the moisture state of the plastic material of unknown moisture state.

Also, according to the gist of a seventh aspect of the present invention, a water removal system for plastic materials, receiving a supply of fixed amount of a plastic material at a time, performing a heat treatment on the plastic material inside a treatment container to remove water inside the plastic material, and conveying the plastic material downstream according to treatment unit, is arranged so that in a measurement passage disposed at a downstream position of the treatment container, plastics of the same type that are of known moisture states and are of at least two different kinds of moisture states are respectively irradiated with electromagnetic waves of a bandwidth of 50 GHz to 1000 GHz from an oscillating apparatus, remaining electromagnetic waves not absorbed by the plastics are measured to acquire a plurality of first measurement values in advance, a function is derived from a relationship of the plurality of first measurement values acquired and the plurality of the moisture states, the plastic of unknown moisture state or a plastic material of unknown moisture state different from the plastic (hereinafter these shall be referred to as the "measured plastic material") is irradiated in the measurement passage with the electromagnetic waves of the bandwidth of 50 GHz to 1000 GHz from the oscillating apparatus, the remaining electromagnetic waves not absorbed by the measured plastic material are measured to acquire a second measurement value, and the second measurement value is applied to the function to compute the moisture state corresponding to the plastic of unknown moisture state.

Also, according to the gist of an eighth aspect of the present invention, in addition to the arrangement of the sixth aspect of the present invention, control is performed so that conveying downstream is not performed when it is judged that the moisture state obtained based on comparison of the first measurement value and the second measurement value does not satisfy being not higher than a predetermined moisture state of the measured plastic material.

Also, according to the gist of a ninth aspect of the present invention, in addition to the arrangement of the sixth aspect of the present invention, control is performed so that when it is judged that the moisture state obtained based on comparison of the first measurement value and the second measurement value does not satisfy being not higher than a predetermined moisture state of the measured plastic material, the plastic material is transported back to an upstream side of the treatment container.

Also, according to the gist of a tenth aspect of the present invention, in addition to the arrangement of any one of the sixth, eighth, and ninth aspects of the present invention, a notifying means is included, which, when it is judged that the moisture state obtained based on comparison of the first measurement value and the second measurement value does not satisfy being not higher than a predetermined moisture state of the measured plastic material, notifies this to an exterior.

Also, according to the gist of an eleventh aspect of the present invention, in addition to the arrangement of the seventh aspect of the present invention, control is performed so that conveying downstream is not performed when it is judged that the moisture state corresponding to the second measurement value, to which the function is applied, does not satisfy being not higher than a predetermined moisture state of the measured plastic material.

Also, according to the gist of a twelfth aspect of the present invention, in addition to the arrangement of the seventh aspect of the present invention, control is performed so that when it is judged that the moisture state corresponding to the second measurement value, to which the function is applied, does not satisfy being not higher than a predetermined moisture state of the measured plastic material, the plastic material is transported back to an upstream side of the treatment container.

Also, according to the gist of a thirteenth aspect of the present invention, in addition to the arrangement of any one of the seventh, eleventh, and twelfth aspects of the present invention, a notifying means is included, which, when it is judged that the moisture state corresponding to the second measurement value, to which the function is applied, does not satisfy being not higher than a predetermined moisture state of the measured plastic material, notifies this to an exterior.

Also, according to the gist of a fourteenth aspect of the present invention, in addition to the arrangement of any one of the sixth to thirteenth aspects of the present invention, the heat treatment of the measured plastic material inside the treatment container accompanies a vacuum drawing process.

With the arrangement of the sixth aspect, first, the plastic material of known moisture state (hereinafter, this plastic shall be referred to as the "reference plastic material") is irradiated in the measurement passage with the electromagnetic waves of the bandwidth of 50 GHz to 1000 GHz from the oscillating apparatus and by measuring the remaining electromagnetic waves not absorbed by the plastic, the first measurement value corresponding to the moisture state of the plastic can be acquired. As a means for obtaining the first measurement value, for example, the above-described Karl Fischer method may be considered.

Thereafter, a plastic, which is of the same material as the reference plastic but is of unknown moisture state, or a plastic material of different material from the reference plastic (hereinafter, this plastic shall be referred to as the "measured plastic material") is irradiated in the measurement passage with electromagnetic waves of the same bandwidth from the oscillating apparatus and the remaining electromagnetic waves not absorbed by the plastic is measured to likewise obtain the second measurement value. The second measurement value and the first measurement value are then compared. That is, the moisture state of the measured plastic material is estimated based on the second measurement value and using the first measurement value as a reference. Generally in converting to data, a difference is obtained.

Here, if the second measurement value is measured under the same conditions as the first measurement value and is equal to the first measurement value, the measured plastic material can be said to be the same in moisture state as the reference plastic. Also, if the values are the same within a margin of error, the measured plastic material may, although depending on the purpose of use, be handled in a manner similar to the reference plastic. Even if the plastics differ in composition, measurement is made possible by providing a coefficient that enables use of the first measurement value. Further, a product check can be performed because it can be made known from the measurement values that the moisture percentage is lower or oppositely the moisture percentage is higher than the reference plastic.

With the arrangement of the seventh aspect, first, each of the reference plastic materials of at least two different kinds is respectively irradiated in the measurement passage with the electromagnetic waves of the bandwidth of 50 GHz to 1000 GHz from the oscillating apparatus and by measuring the remaining electromagnetic waves not absorbed by the plastics, the plurality of first measurement value corresponding to the moisture states of the plastic can be acquired, and a function can be derived from the relationship between the plurality of first measurement values and the plurality of moisture states. As a means for obtaining the plurality of first measurement values, for example, the above-described Karl Fischer method may be considered.

Thereafter, the measured plastic material is irradiated in the measurement passage with the electromagnetic waves of the same bandwidth as the above from the oscillating apparatus and the remaining electromagnetic waves not absorbed by the plastic are measured to likewise obtain the second measurement value. The second measurement value is then applied to the function to compute the moisture state corresponding to the measured plastic material.

It thus becomes possible to judge the moisture state of the measured plastic based on a position of the second measurement value on the function, or any point on the function may be used as a reference value and the moisture state can be judged based on a relationship of the second measurement value with respect to the reference point.

For example, suppose a first-order function, expressed by f(x)=ax+b, is derived based on the plurality of first measurement values. By substituting the second measurement value in x, the f(x) that is the moisture state of the plastic of unknown moisture state is determined. Also, by judging whether the second measurement value is large or small with respect to a reference value on f(x) that is not a first measurement value, a product check can be performed because it can be made known that the moisture percentage is lower or oppositely the moisture percentage is higher than the reference value.

It is thus possible to rapidly measure whether or not the measured plastic material subject to the heat treatment inside the treatment container is in a predetermined dry state.

Also preferably, control is performed so that conveying downstream is not performed when it is judged that the moisture state of the measured plastic material obtained based on the second measurement value does not satisfy being not higher than the predetermined moisture state of the measured plastic material. This is performed to avoid use of a plastic with which a degree of drying is not adequate.

Also in the above, preferably, control is performed so that when it is judged that the moisture state of the measured plastic material obtained based on the second measurement value does not satisfy being not higher than the predetermined moisture state of the measured plastic material, the plastic material is transported back to the upstream side of the treatment container. This is performed to return the material back to the drying process.

Also in the above, preferably, when it is judged that the moisture state of the measured plastic material obtained based on the second measurement value does not satisfy being not higher than a predetermined moisture state of the measured plastic material, this is notified to the exterior by the notifying means. A worker can thereby readily recognize that adequate drying was not performed.

Also in the above, it is preferable in terms of drying speed and an improvement in drying degree that the heat treatment of the measured plastic material inside the treatment container accompanies a vacuum drawing process.

Although in the above, it is preferable in terms of simplification of calculation and accuracy of numerical values that the measurement conditions under which the first measurement value is acquired and the measurement conditions under which the second measurement value is acquired are the same, if a difference of the measurement conditions can be applied to the second measurement value by some form of function value, the measurement conditions for obtaining the two measurement values may differ.

The remaining electromagnetic waves resulting from irradiation of the electromagnetic waves of the bandwidth of 50 GHz to 1000 GHz are used as a parameter of the moisture state because electromagnetic waves of the bandwidth of 50 GHz to 1000 GHz (that is, terahertz waves and millimeter waves) have a property of being absorbed by water and yet does not cause the water to boil nor influence a physical property of a plastic even upon irradiation onto the plastic. An absorption amount is based on a positive correlation with the water content in the plastic, that is, on a property that the larger the amount of water in the plastic, the more the radio waves are absorbed. The remaining electromagnetic waves after absorption are in a negative correlation with the water content in the plastic.

As the plastic, both thermosetting and thermoplastic plastics can be measured as long as the plastic has a water absorbing characteristic. Also, a shape of the plastic does not matter. Although a pellet shape may be considered for the material, any of various shapes may be considered for a plastic that has been made into a product.

Effect(s) of the Invention

By the first to fifth aspects of the invention, a moisture state of a plastic material of unknown moisture state can be measured rapidly.

By the sixth to fourteenth aspects of the invention, in addition to the above effect, a moisture state of a dried plastic material can be measured rapidly and a plastic material of inadequate drying can be rejected.

MODE(S) FOR CARRYING OUT THE INVENTION

Examples in which the present invention is embodied shall now be described with reference to the drawings.

Example 1

Figure 1:
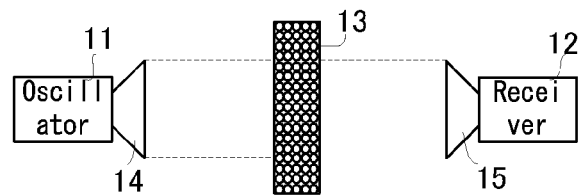
FIG. 1 is a schematic view of Example 1 according to the present invention.

FIG. 1 is a schematic view of an apparatus used in the present example.

A plastic 13, which is to be measured, is disposed along a path of an oscillator 11 and a receiver 12. The plastic 13 is housed, for example, in a tray, etc., made of stainless steel, through which radio waves can be transmitted and which does not absorb water, in a case where the plastic 13 has a shape that is granular or powderous and is set as it is on a stable base in a case where the plastic 13 has a large outer shape that enables it to stand on its own. The oscillator 11 is arranged from an unillustrated oscillating circuit, amplifying circuit, control unit, operation unit, etc., and irradiates terahertz waves of a predetermined frequency from a horn antenna 14 with directivity. The receiver 12 is arranged from an unillustrated receiving circuit, amplifying circuit, control unit, operation unit, etc., and receives radio waves from a horn antenna 15 with directivity. In Example 1, the terahertz waves generated from the oscillator 11 are irradiated onto the plastic 13 and made to be absorbed by the plastic 13 and remaining terahertz waves that are transmitted without being absorbed are received and measured by the receiver 12.

A method for detecting in water in plastics that is executed by the apparatus of the above arrangement shall now be described.

1. Measurement in a Default State

First, the terahertz waves from the oscillator 11 are received by the receiver 12 in a state where a plastic 13 is not disposed in between and a received amount in the default state without absorption of terahertz waves due to a plastic 13 is measured just in case.

2. Measurement of a Reference Plastic

A moisture percentage of a plastic 13 is measured by the Karl Fischer method, and using this plastic 13 of known moisture percentage as a reference plastic, the terahertz waves are irradiated from the oscillator 11 and made to be absorbed by the plastic 13 and the remaining terahertz waves are received by the receiver 12 to measure a first measurement value. The measurement value is obtained as a transmission intensity.

The absorption amount of the absorbed terahertz waves is computed by subtracting the measurement value of the measured remaining terahertz waves from the measurement value in the default state.

3. Measurement of a Measured Plastic

Thereafter, a plastic 13 of unknown moisture percentage is used as a measured plastic, the terahertz waves are irradiated from the oscillator 11 and made to be absorbed by the plastic 13, and the remaining terahertz waves are received by the receiver 12 to measure a second measurement value, which is collated with the first measurement value of the reference plastic. For example, if the second measurement value is equal to or is equal within a fixed margin of error to the measurement value of the reference plastic, it may be handled as corresponding to the same moisture percentage as the reference plastic. Or, it can be known from the numerical values that the moisture percentage is lower or oppositely the moisture percentage is higher than that of the reference plastic and a product check can thus be performed.

Also, the reference plastic and the measured plastic may be of the same composition (material) or may differ in composition. This is because, if, for example, the plastics are comparatively similar in properties, the plastics can be handled as being the same, and even if the plastics differ, a coefficient that corrects for a direction (vector) of the difference may be provided and applied to the value of the reference plastic. The same applies to the following examples.

Example 2

Figure 2:
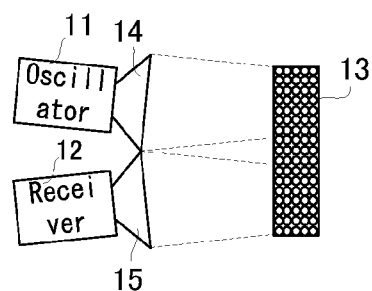
FIG. 2 is a schematic view of Example 2.

FIG. 2 shows a variation of the apparatus of Example 1. Example 2 has an arrangement where the oscillator 11 and the receiver 12 are disposed adjacently and a plastic 13 is disposed in a predetermined position in a front direction of the horn antennas 14 and 15 of the oscillator 11 and the receiver 12. The horn antennas 14 and 15 are adjusted to be in a slightly inwardly directed angle in accordance with a reflection angle. This is because with the apparatus of Example 2, reflected waves due to irradiation of the plastic 13 with the terahertz waves are in a negative correlation with an absorptivity of the terahertz waves in the plastic 13 and there is a trend that as the moisture percentage of the plastic 13 increases, the reflected waves decrease, and as the moisture percentage decreases, the reflected waves increase in a relative manner.

The same measurements as those of Example 1 are possible with such an apparatus.

Example 3

Figure 3:
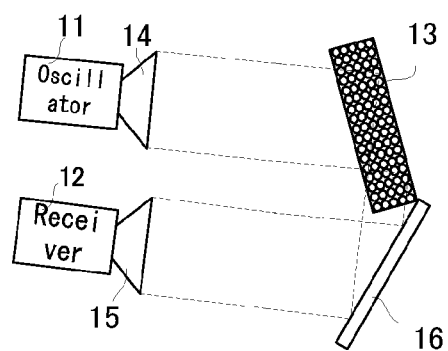
FIG. 3 is a schematic view of Example 3.

FIG. 3 shows a variation of the apparatuses of Examples 1 and 2. Example 3 has an arrangement where the oscillator 11 and the receiver 12 are disposed adjacently and a plastic 13 is disposed in a predetermined position in a front direction of the horn antennas 14 and 15 of the oscillator 11 and the receiver 12. A scattering plate 16 is disposed at a side of the plastic 13. The apparatus of Example 3 is arranged so that the terahertz waves are scattered inside the plastic and the scattered waves are reflected by the scattering plate 16 and directed in the direction of the horn antenna 15 of the receiver 12. This is because like the reflected waves, the scattered waves are in a negative correlation with an absorptivity of the terahertz waves in the plastic 13 and there is a trend that as the moisture percentage of the plastic 13 increases, the scattered waves decrease, and as the moisture percentage decreases, the scattered waves increase in a relative manner.

The same measurements as those of Example 1 are possible with such an apparatus as well.

Example 4

Example 4, with which Example 1 is embodied more specifically, shall now be described.

Figure 4:
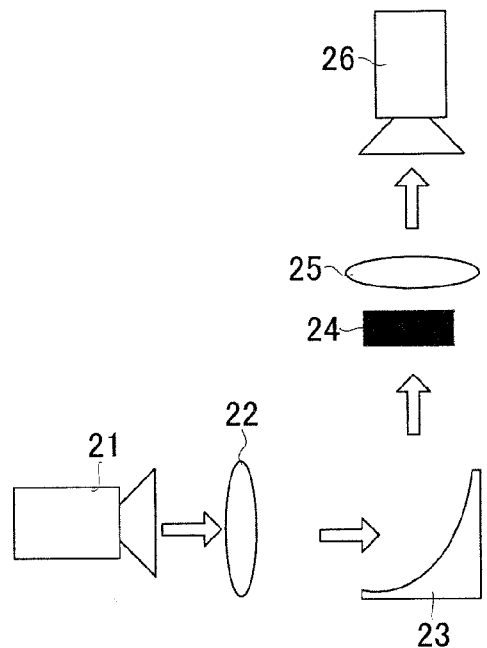
FIG. 4 is a schematic view of Example 4.

FIG. 4 is a schematic view of the apparatus used in the present example. A first lens 22, a parabolic mirror 23, a sample case 24, a second lens 25, and a receiver 26 are disposed in series along an irradiation path of an oscillator 21 that irradiates terahertz waves.

The oscillator 21 is arranged from an unillustrated oscillating circuit, amplifying circuit, control unit, operation unit, etc., and irradiates terahertz waves of a predetermined frequency from a horn antenna with directivity. The first lens 22 adjusts the radially dispersing terahertz waves generated from the horn antenna to a parallel emission direction. The parabolic minor 23 changes the emission direction (by 90 degrees in the present example) while suppressing attenuation of the terahertz waves. A plurality of parabolic minors may be disposed as necessary.

Granular plastic that is to be measured is sealed inside the sample case 24.

A method for detecting in water in plastics that is executed by the apparatus of the above arrangement shall now be described.

In Example 4, three kinds of granular acrylic resins A to C that differ only in moisture percentage were prepared. Two kinds or no less than four kinds may be used instead freely. The moisture percentages of the acrylic resins A to C were measured by the Karl Fischer method. Terahertz waves of a wavelength of 94 GHz were irradiated from the oscillator 21 onto each of the acrylic resins A to C by the same operation as that of Example 1 and the first measurement value (transmission intensity) was obtained for each resin A to C. The results are shown in Table 1. In Table 1, an absorption amount is obtained by subtracting the transmission intensity from a blank value.

Figure 8:
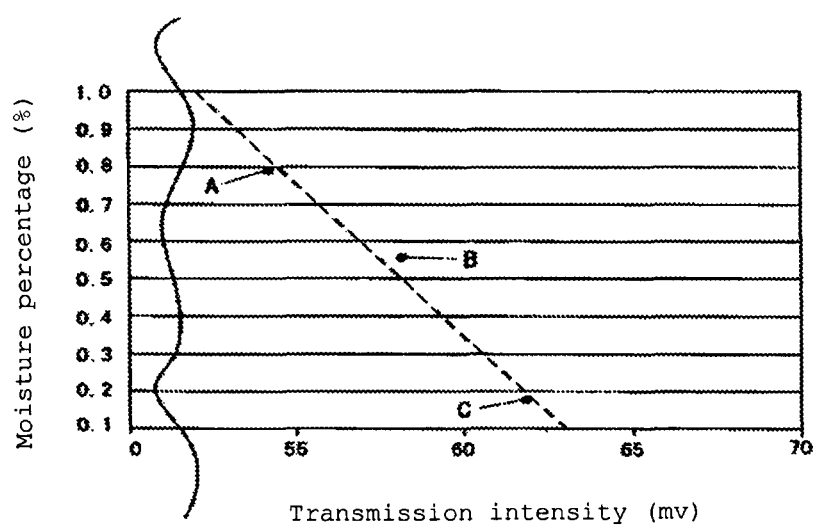
FIG. 8 is a graph illustrating the relationship between the terahertz wave transmission intensity and the moisture percentage of an acrylic resin.

Based on the results of Table 1, a correlation for the present acrylic resin is obtained in the relationship between the terahertz wave transmission intensity and the moisture percentage of the acrylic resin as shown in FIG. 8. The transmission intensity and the moisture percentage are generally neatly correlated. By determining standard deviations for these values and executing normalization to adjust the scattering, a $$\text{first-order function: } f(x)=ax+b$$

can be derived. A broken line in FIG. 8 is an image of the first-order function. Here, a and b are unique variables determined by the plastic to be measured, the wavelength of the terahertz waves, and other measurement conditions.

By then determining, under the same conditions, the second measurement value (transmission intensity) for another granular acrylic resin that differs only in moisture percentage and applying it to f(x), the moisture percentage of the acrylic resin of unknown moisture percentage can be computed accurately. Also, if a moisture percentage that is to be a reference is to be set, by setting it at any point on f(x), the transmission intensity, that is, the measurement value corresponding to the moisture percentage can be obtained at the same time. Also, any point on f(x) may be used as a reference value to judge whether the second measurement value is large or small with respect to the reference value.

By this arrangement, rapid and accurate moisture percentage measurement of a plastic is made possible, not only for a simple judgment of being low or high with respect to a certain moisture percentage but also in a case of measurement where a predetermined range of moisture percentage must be satisfied. Also, the moisture percentage of an unknown acrylic resin can be computed using, as a reference value, any point on the first-order function that has not actually been measured.

TABLE 1

| | Measurement method | | |
|---|---|---|---|
| | Measurement by receiver (94 GHz) | | Measurement by Karl Fischer method |
| Measured sample | Transmission intensity (mv) | Absorption amount (mv) | Moisture percentage (%) |
| A | 54.797 | 17.873 | 0.790 |
| B | 57.751 | 14.919 | 0.535 |
| C | 62.109 | 10.561 | 0.188 |

Example 5

Example 5, with which Example 1 to Example 4 are embodied more specifically shall now be described.

Figure 5:
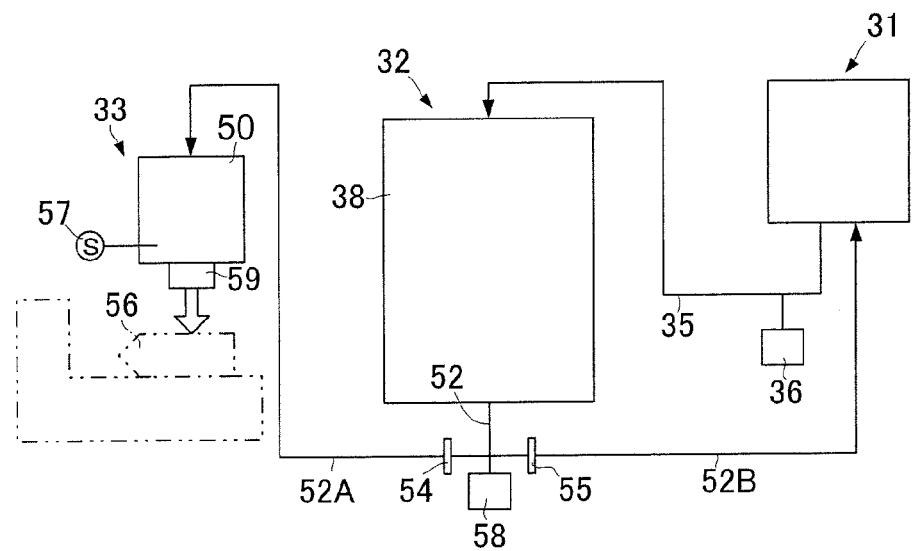
FIG. 5 is a schematic view of a supplying unit of Example 5.

FIG. 5 is a simplified schematic view of a plastic material supplying system (hereinafter referred to as "supplying system") of Example 5. A plastic material supplying system is arranged from a tank apparatus 31 housing a plastic material of pellet form, a drying apparatus 32 as a water removal system that receives the supply of plastic material from the tank apparatus 31 and performs heated drying of the plastic material, and a molding machine 33 that receives the supply of the dried plastic material and molds a molded product.

The tank apparatus 31 houses the plastic material basically in a manner such that external air is not introduced and the plastic material is supplied to the drying apparatus 32 via a flexible hose 35 by driving of a blower apparatus 36.

Figure 6:
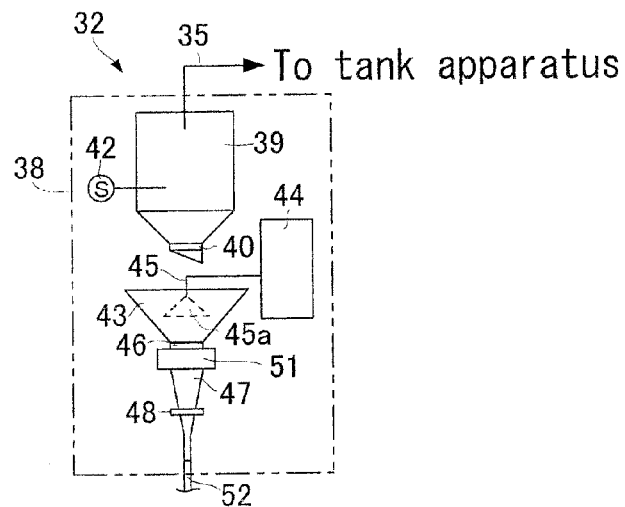
FIG. 6 is a schematic view for describing an internal arrangement of a drying apparatus of Example 5.
Figure 7:
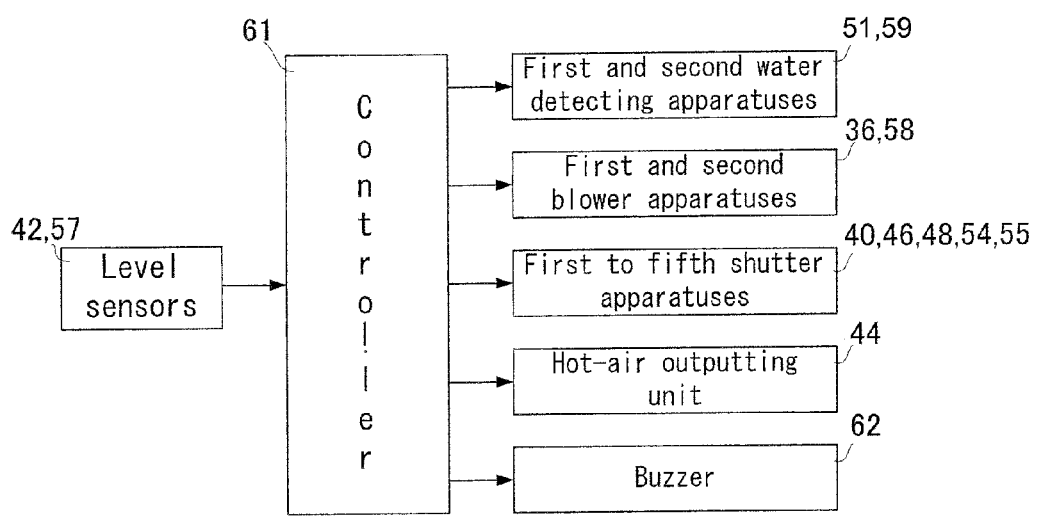
FIG. 7 is a block diagram for describing an electrical arrangement of the supplying unit of Example 5.

As shown in FIG. 6, the drying apparatus 32 includes a hopper 39 at an upper position of an interior of a housing 38. The flexible hose 35 from the tank apparatus 31 is connected to the hopper 39. A first shutter apparatus 40 is disposed at a lower position of the hopper 39 and a shutter is enabled to open and close by means of an unillustrated air cylinder that is provided adjacently. A fixed amount of plastic material is discharged downward by opening of the first shutter apparatus 40 for a fixed amount of time. A level sensor 42 that detects a storage state of the plastic material is provided adjacent to the hopper 39. A heating hopper 43 is disposed as a treatment container at a position below the hopper 39. Inside the heating hopper 43 is disposed a head 45a of a hot-air introducing duct 45 connected to a hot-air outputting unit 44 arranged from a heater and a blower and the plastic material housed inside the heating hopper 43 is heated thereby. A second shutter apparatus 46 is disposed at a lower position of the heating hopper 43 and a shutter is enabled to open and close by means of an unillustrated air cylinder that is provided adjacently. An accumulator 47 is formed at a position below and adjacent to the second shutter apparatus 46. A third shutter apparatus 48 is disposed at a lower position of the accumulator 47 and a shutter is enabled to open and close by means of an unillustrated air cylinder that is provided adjacently. The accumulator 47 forms a through passage for the plastic material that is heat-dried inside the heating hopper 43 and also temporarily stores the plastic material supplied from the heating hopper 43 in a state where the third shutter apparatus 48 is closed. A first water detecting apparatus 51 including the oscillator and the receiver of the present invention as an assembly is disposed at an upper position of the accumulator 47. A base end of a flexible hose 52 in communication with an exterior of the housing 38 is connected to a lower end of the accumulator 47.

The molding machine 33 is arranged from a hopper 50 that is sealed basically so that external air is not introduced and a molding machine main body 56. A level sensor 57 that detects a storage state of the plastic material is provided adjacent to the hopper 50. A second water detecting apparatus 59 including the oscillator and the receiver of the present invention as an assembly is disposed at a lower position (an unillustrated passage position) of the hopper 50.

At an exterior of the housing 38, the flexible hose 52 branches into first and second branch hoses 52A and 52B, the first branch hose 52A is connected to the hopper 50, and the second branch hose 52B is connected to the tank apparatus 31. In a vicinity of the branching of the flexible hose 52, fourth and fifth shutter apparatuses 54 and 55 are respectively disposed across a branching point. The plastic material inside the accumulator 47 is delivered to the direction of either the first or second branch hose 52A or 52B by driving of a blower apparatus 58. In Example 5, each of the fourth and fifth shutter apparatuses 54 and 55 causes, in accordance with turning on/off of unillustrated limit switches, a shutter to advance to a corresponding position facing the branch hose 52A or 52B to restrict the passage of the plastic material. Thus, in a state where the fourth shutter apparatus 54 is opened and the fifth shutter apparatus 55 is closed, the plastic material is delivered in the direction of the molding machine 33 and oppositely in a state where the fourth shutter apparatus 54 is closed and the fifth shutter apparatus 55 is opened, the plastic material is delivered in the direction of the tank apparatus 31.

An electrical arrangement related to control of the supplying system arranged as described above shall now be described. The supplying system includes a controller 61, which is a control apparatus. The first and second water detecting apparatuses 51 and 59, the blower apparatuses 36 and 58, the level sensors 42 and 57, the first to fifth shutter apparatuses 40, 46, 48, 54, and 55, the hot-air outputting unit 44, and a buzzer 61 as a notifying means are connected to the controller 61. The controller 61 basically executes control based on detection values of the level sensors 42 and 57 based on programs stored in a memory.

Also, specifically with the present invention, relationships among various plastic materials, terahertz wave absorption characteristics according to material, and moisture percentages of the plastic materials under respective measurement conditions of the water detecting apparatuses 51 and 59 are stored in the memory inside the controller 61. Specifically, it may be considered that a transmission intensity, corresponding to a certain moisture percentage that is a threshold value on a first-order function such as that of Example 4, is used as a reference value and whether or not a value is larger than the reference value is judged. Or, it may be considered that a transmission intensity of a plastic material of known moisture percentage such as that in any of Examples 1 to 3 is used as a reference value and whether or not a value is larger than the reference value is judged. In Example 5, if a value no less than the reference value cannot be detected at the receiving side in each of the water detecting apparatuses 51 and 59, it is judged that a predetermined degree of drying has not been attained.

An outline of the control executed by the controller 61 shall be described below together with the operation of the supplying system.

Control Between the Tank Apparatus and the Drying Apparatus

When based on a detection signal of the level sensor 42 at the drying apparatus 32 side, it is judged that the amount of the plastic material stored in the hopper 39 inside the drying apparatus 32 is low, the controller 61 controls the tank apparatus 31 side to replenish the material.

The controller 61 drives the blower apparatus 36 for a fixed amount of time to make the plastic material be supplied from the tank apparatus 31 to the hopper 39.

Control Between the Drying Apparatus and the Molding Machine

When based on a detection signal of the level sensor 57 at the molding machine 33 side, it is judged that the amount of the plastic material stored in the hopper 50 inside the molding machine 33 is low, the controller 61 controls the drying apparatus 32 side to replenish the material.

A) First, if the controller 61 judges from a past history of opening of the second shutter apparatus 46 and states of the fourth and fifth shutter apparatuses 54 and 55 that there is plastic material inside the accumulator 47, opening and closing of the third shutter apparatus 48 are executed to make all of the plastic material inside the accumulator 47 flow down in the direction of the flexible hose 52. At the same time, the fourth shutter apparatus 54 side is opened, the fifth shutter apparatus 55 side is closed, and the blower apparatus 58 is driven for a fixed amount of time to deliver all of the plastic material to the first branch hose 52A side.

B) Then, in order to dry the plastic material of a subsequent lot, the controller 61 executes the opening and closing of the first shutter apparatus 40 at a set timing to make a fixed amount of the plastic material drop from the hopper 39 into the heating hopper 43. The hot-air outputting unit 44 is then driven under time and temperature conditions set in advance to dry the plastic material. At the stage at which the drying time has elapsed, the controller executes the opening and closing of the second shutter apparatus 46 to make the plastic material, with which the drying has ended, drop into the accumulator 47.

C) Then, in accordance with the timing of dropping, the controller 61 drives the first water detecting apparatus 51 to execute water detection of the plastic material passing through the accumulator 47.

Here, if the detection result is that the plastic material inside the accumulator 47 is not of a predetermined moisture percentage or less, that is, the drying in the drying apparatus 32 is not adequate for use in the molding machine 33, this is notified by the buzzer, and after closing the second shutter apparatus 46, opening and closing of the third shutter apparatus 48 are executed to drop all of the plastic material inside the accumulator 47 into the flexible hose 52. At the same time, the fifth shutter apparatus 55 is opened, the fourth shutter apparatus 54 is closed, and the blower apparatus 58 is driven for a fixed amount of time to deliver (return) all of the plastic material to the tank apparatus 31 side.

D) On the other hand, if as a result of water detection by the first water detecting apparatus 51, it is judged that the drying at the drying apparatus 32 is adequate, either of the following two processes is performed.

i) If based on a detection signal from the level sensor 57, it is judged that the amount of the plastic material stored in the hopper 50 inside the molding machine 33 is still low, all of the plastic material is delivered to the first branch hose 52A side in the same manner as in A) described above, and then a transition to B) is performed.

ii) If there is no detection signal from the level sensor 57, standby in the state of storage inside the accumulator 47 is performed temporarily.

E) On the other hand, if in A), the controller 61 judges, from the previous history of opening of the second shutter apparatus 46 and the states of the fourth and fifth shutter apparatuses 54 and 55, that there is no plastic material inside the accumulator 47, that is, judges that the previous drying was not adequate and the corresponding lot has been returned to the tank apparatus 31, the opening and closing of the first shutter apparatus 40 are executed and the plastic material of the fixed amount is dropped into the heating hopper 43. The plastic material is then dried by driving the hot-air outputting unit 44 for a longer time than the heating time in the immediately previous drying process (for example, the time is automatically extended to 120% of the previous time). Then at the stage at which the newly set time has elapsed, the controller 61 executes the opening and closing of the second shutter apparatus 46 to make the plastic material, with which the drying has ended, drop into the accumulator 47. Instead of automatically extending the drying time as described above, the time and heating temperature may be set anew from an input means. During dropping into the accumulator 47, the controller 61 executes the processes of C) and D) described above.

F) Also, with regard to the plastic material that has been stored in the hopper 50 of the molding machine 33 via the first branch hose 52A in A), the controller 61 drives the first water detecting apparatus 51 at a predetermined timing (for example, every 5 minutes) to execute water detection of the plastic material guided in the direction of the molding machine main body 56. Whether or not the plastic material is in the predetermined dry state can thereby be checked even at a final stage.

By having the above arrangement, the supplying system of Example 5 exhibits the following effects.

(1) A defective percentage can be reduced extremely because the moisture content of the plastic material can be measured in real time in an actual apparatus and thereby be reflected in the product.

(2) Whether or not the moisture content of a plastic material that is a molding material is no more than a fixed amount can be checked at respective stages of the tank apparatus 31, the drying apparatus 32, and the molding machine 33 and thus plastic material that is inappropriate as molding material can be rejected reliably.

(3) Conventionally, even if a product is viewed and it is judged from the finished quality that the moisture content of the plastic material was high, it cannot be known at what stage the material became inappropriate and thus all of the plastic material that could be the cause must be judged as being defective. However, it can be asserted that the moisture content of a certain lot is inappropriate based on numerical values as described above and thus there is no need to wastefully discard raw materials and a cause can be determined at an early stage to carry out countermeasures with expedition.

(4) Unlike with the Karl Fischer method, the plastic material subject to measurement can be used as it is as the actual material and thus the plastic material is not wasted for measurement.

The present invention may also be embodied as follows.

Although in Example 4, the first-order function was determined by normalizing based on actually measurement values, in a case where normalization does not have to be performed, the first-order function may be computed by determining an average value. In a case where only two points are measured, there is also no need to determine an average value.

Although in Example 5, from a standpoint that it is preferable for the plastic material to be dry in any case, the controller 61 considers a certain reference value to be a threshold value in the water detection by the first water detecting apparatus 51 as well on a basis that a moisture percentage is low if a measurement value is larger than the reference value, in a case where "a predetermined moisture percentage is preferable," a first-order function such as that of Example 4 may be obtained and control may be performed so that a measurement value falls between two reference values along the straight line of the function.

In Example 5, a water detecting apparatus may also be provided in the tank apparatus 31. In this case, a design is possible where if it judged that the plastic material is drier than a certain value, it can be delivered directly to the molding machine 33 without being delivered to the drying apparatus 32.

Although with the structure in Example 5 described above, the plastic material is fed by the blower apparatuses 36 and 58, feeding may be performed instead by a vacuum suction system using an air pump apparatus.

Welded ducts may be used instead of flexible hoses 35 and 52 for delivering the plastic material.

Although in Example 5 described above, the plastic material is returned to the tank apparatus 31 when the moisture content is high, an arrangement is also possible where the plastic material is discharged to the exterior from the accumulator 47 without being returned (obviously without being delivered to the molding machine 33 side).

Although in Example 5 described above, the plastic material is returned to the tank apparatus 31 when the moisture content is high, an arrangement is also possible where the plastic material is returned to the hopper 39.

The arrangement and control of the supplying system of Example 5 described above are those of a single example and these may be realized in other arrangements as well.

Although with Example 5 described above, a heating dryer was cited as an example, the heating apparatus 32 may instead be arranged as a water removal system of a type with which vacuum drawing is performed at the same time as heating to improve the degree of dryness.

The present invention may be carried out in other modes with changes being made within a range not falling outside the gist thereof.

DESCRIPTION OF THE SYMBOLS

11 . . . oscillator as an oscillating apparatus, 12 . . . receiver as a receiving apparatus, 35 . . . flexible hose as a measurement passage, 51, 57 . . . water detecting apparatus as an oscillating apparatus and a receiving apparatus, 43 . . . hopper type housing dish as a treatment container, 47 . . . accumulator as a measurement passage.

The invention claimed is:

1. A method for detecting water in plastics, comprising the steps of irradiating a plastic of known moisture state with electromagnetic waves of a bandwidth of 50 GHz to 1000 GHz from an oscillating apparatus, measuring remaining electromagnetic waves not absorbed by the plastic to acquire a first measurement value in advance, irradiating the plastic of unknown moisture state or a plastic of unknown moisture state different from the plastic (hereinafter these shall be referred to as the "measured plastic") with the electromagnetic waves of the bandwidth of 50 GHz to 1000 GHz from the oscillating apparatus, measuring the remaining electromagnetic waves not absorbed by the measured plastic to acquire a second measurement value, and comparing the first measurement value and the second measurement value to compute the moisture state of the plastic of unknown moisture state.

2. A method for detecting water in plastics, comprising the steps of respectively irradiating plastics of the same type that are of known moisture states and are of at least two different kinds of moisture states with electromagnetic waves of a bandwidth of 50 GHz to 1000 GHz from an oscillating apparatus, measuring remaining electromagnetic waves not absorbed by the plastics to acquire a plurality of first measurement values in advance, deriving a function from a relationship between the plurality of first measurement values acquired and the plurality of moisture states, irradiating the plastic of unknown moisture state or a plastic of unknown moisture state different from the plastic (hereinafter these shall be referred to as the "measured plastic") with the electromagnetic waves of the bandwidth of 50 GHz to 1000 GHz from the oscillating apparatus, measuring the remaining electromagnetic waves not absorbed by the measured plastic to acquire a second measurement value, and applying the second measurement value to the function to compute the moisture state corresponding to the plastic of unknown moisture state.

3. The method for detecting water in plastics according to claim 1, wherein the first or second measurement value is measured by making the electromagnetic waves generated from the oscillating apparatus be transmitted through the plastic and be received by a receiving apparatus disposed at a rear side of the plastic.

4. The method for detecting water in plastics according to claim 2, wherein the first or second measurement value is measured by making the electromagnetic waves generated from the oscillating apparatus be transmitted through the plastic and be received by a receiving apparatus disposed at a rear side of the plastic.

5. The method for detecting water in plastics according to claim 1, wherein the first or second measurement value is measured by making the electromagnetic waves generated from the oscillating apparatus be reflected inside the plastic and making the reflected waves be received by a receiving apparatus.

6. The method for detecting water in plastics according to claim 2, wherein the first or second measurement value is measured by making the electromagnetic waves generated from the oscillating apparatus be reflected inside the plastic and making the reflected waves be received by a receiving apparatus.

7. The method for detecting water in plastics according to claim 1, wherein the first or second measurement value is measured by making the electromagnetic waves generated from the oscillating apparatus be scattered inside the plastic and making the scattered waves be received by a receiving apparatus.

8. The method for detecting water in plastics according to claim 2, wherein the first or second measurement value is measured by making the electromagnetic waves generated from the oscillating apparatus be scattered inside the plastic and making the scattered waves be received by a receiving apparatus.

9. A water removal system for plastic materials, receiving a supply of a fixed amount of a plastic material at a time, performing a heat treatment on the plastic material inside a treatment container to remove water inside the plastic material, and conveying the plastic material downstream according to treatment unit, and
wherein a plastic material of known moisture state is housed in a measurement passage disposed at a downstream position of the treatment container and irradiated with electromagnetic waves of a bandwidth of 50 GHz to 1000 GHz from an oscillating apparatus, remaining electromagnetic waves not absorbed by the plastic material are measured to acquire a first measurement value in advance, the plastic of unknown moisture state or a plastic material of unknown moisture state different from the plastic (hereinafter these shall be referred to as the "measured plastic material") is irradiated in the measurement passage with the electromagnetic waves of the bandwidth of 50 GHz to 1000 GHz from the oscillating apparatus, the remaining electromagnetic waves not absorbed by the measured plastic material are measured to acquire a second measurement value, and the first measurement value and the second measurement value are compared to compute the moisture state of the plastic material of unknown moisture state.

10. A water removal system for plastic materials, receiving a supply of fixed amount of a plastic material at a time, performing a heat treatment on the plastic material inside a treatment container to remove water inside the plastic material, and conveying the plastic material downstream according to treatment unit, and
wherein in a measurement passage disposed at a downstream position of the treatment container, plastics of the same type that are of known moisture states and are of at least two different kinds of moisture states are respectively irradiated with electromagnetic waves of a bandwidth of 50 GHz to 1000 GHz from an oscillating apparatus, remaining electromagnetic waves not absorbed by the plastics are measured to acquire a plurality of first measurement values in advance, a function is derived from a relationship between the plurality of first measurement values acquired and the plurality of moisture states, the plastic of unknown moisture state or a plastic material of unknown moisture state different from the plastic (hereinafter these shall be referred to as the "measured plastic material") is irradiated in the measurement passage with the electromagnetic waves of the bandwidth of 50 GHz to 1000 GHz from the oscillating apparatus, the remaining electromagnetic waves not absorbed by the measured plastic material are measured to acquire a second measurement value, and the second measurement value is applied to the function to compute the moisture state corresponding to the plastic of unknown moisture state.

11. The water removal system for plastic materials according to claim 9, wherein control is performed so that conveying downstream is not performed when it is judged that the moisture state obtained based on comparison of the first measurement value and the second measurement value does not satisfy being not higher than a predetermined moisture state of the measured plastic material.

12. The water removal system for plastic materials according to claim 9, wherein control is performed so that when it is judged that the moisture state obtained based on comparison of the first measurement value and the second measurement value does not satisfy being not higher than a predetermined moisture state of the measured plastic material, the plastic material is transported back to an upstream side of the treatment container.

13. The water removal system for plastic materials according to claim 9, comprising a notifying means, which, when it is judged that the moisture state obtained based on comparison of the first measurement value and the second measurement value does not satisfy being not higher than a predetermined moisture state of the measured plastic material, notifies this to an exterior.

14. The water removal system for plastic materials according to claim 10, wherein control is performed so that conveying downstream is not performed when it is judged that the moisture state corresponding to the second measurement value, to which the function is applied, does not satisfy being not higher than a predetermined moisture state of the measured plastic material.

15. The water removal system for plastic materials according to claim 10, wherein control is performed so that when it is judged that the moisture state corresponding to the second measurement value, to which the function is applied, does not satisfy being not higher than a predetermined moisture state of the measured plastic material, the plastic material is transported back to an upstream side of the treatment container.

16. The water removal system for plastic materials according to claim 10, comprising a notifying means, which, when it is judged that the moisture state corresponding to the second measurement value, to which the function is applied, does not satisfy being not higher than a predetermined moisture state of the measured plastic material, notifies this to an exterior.

17. The water removal system for plastic materials according to claim 9, wherein the heat treatment of the measured plastic material inside the treatment container accompanies a vacuum drawing process.

18. The water removal system for plastic materials according to claim 10, wherein the heat treatment of the measured plastic material inside the treatment container accompanies a vacuum drawing process.

* * * * *